Figure 1:
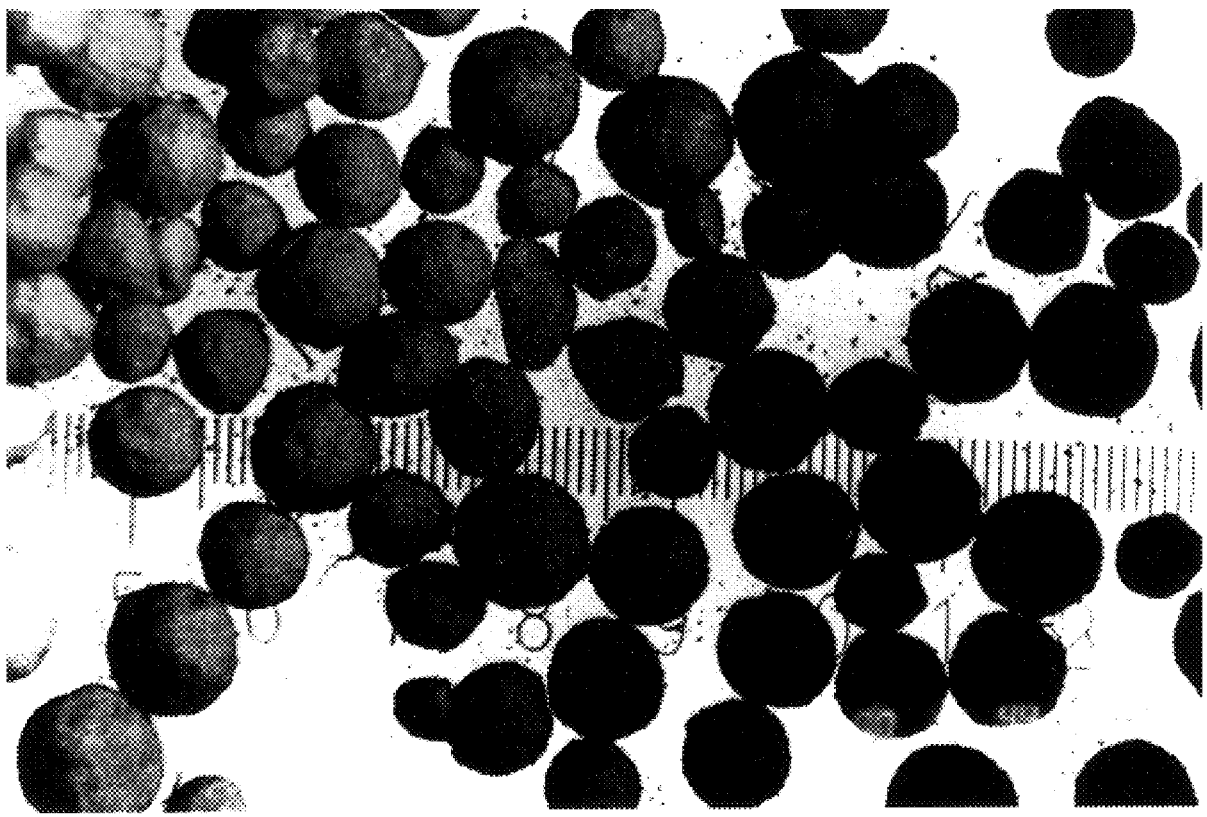

United States Patent [19]
Carencotte et al.

[11] Patent Number: 5,994,538
[45] Date of Patent: Nov. 30, 1999

[54] SPHERICAL 10-PHENOTHIAZINYLPROPANOIC ACID AGGLOMERATES AND METHOD FOR PREPARING SAME

[75] Inventors: Frédéric Carencotte, Caluire et Cuire; Philippe Marchal, Grézieu-la-Varenne; Jean-Claude Savet, Brignais, all of France

[73] Assignee: Rhodia Chimie, Courbevoie Cedex, France

[21] Appl. No.: 09/142,472

[22] PCT Filed: Mar. 7, 1997

[86] PCT No.: PCT/FR97/00405

§ 371 Date: Nov. 24, 1998

§ 102(e) Date: Nov. 24, 1998

[87] PCT Pub. No.: WO97/32864

PCT Pub. Date: Sep. 12, 1997

[30] Foreign Application Priority Data

Mar. 7, 1996 [FR] France .................................. 96 03114

[51] Int. Cl.$^6$ .......................... C07D 279/20; C07B 45/04
[52] U.S. Cl. .................................. 544/35; 544/36; 544/38
[58] Field of Search ................................... 544/35, 36, 38

[56] References Cited

U.S. PATENT DOCUMENTS 3,160,630  12/1964  Vierling .................................. 260/243
3,555,156  1/1971  Kviesitis et al. ......................... 424/247

OTHER PUBLICATIONS

Journal of Heterocyclic Chemistry, vol. 9, No. 2, Apr. 1972, pp. 325–330, XP002017108, Sister M.C. Malmstrom et al, "The crystal and molecular structure of phenothiazine–10–propionic acid".

Journal of Organic Chemistry, vol. 15, No. 5, Sep. 1950, Easton US, pp. 1125–1130, XP002017100 N.L. Smith: "Synthesis of phenothiazine derivatives for use as antioxidants".

*Primary Examiner*—Mukund J. Shah
*Assistant Examiner*—Pavanaram K Sripada
*Attorney, Agent, or Firm*—Burns, Doane, Swecker & Mathis, L.L.P.

[57] ABSTRACT

The present invention relates to novel spherical agglomerates of 10-phenothiazinylpropanoic acid. The invention also relates to a process for obtaining those agglomerates.

The process for preparing the spherical agglomerates of 10-phenothiazinylpropanoic acid is characterized by stirring a suspension of 10-phenothiazinylpropanoic acid in water in the presence of a binder liquid which is not miscible with water selected from esters of aliphatic or cycloaliphatic acids, aliphatic or cycloaliphatic alcohols, and aliphatic or cycloaliphatic ketones.

22 Claims, 1 Drawing Sheet

SPHERICAL 10-PHENOTHIAZINYLPROPANOIC ACID AGGLOMERATES AND METHOD FOR PREPARING SAME

The present invention relates to novel spherical agglomerates of 10-phenothiazinylpropanoic acid. The invention also relates to a process for obtaining those agglomerates.

10-phenothiazinylpropanoic acid is an organic product used as an intermediate in synthesis.

It is represented by the following formula

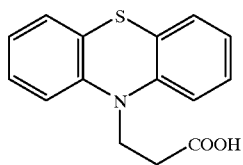

A method for preparing that product is described by Nathan L., Smith J. in Org. Chem 15, 1125 (1950).

The product obtained is in the form of a precipitate which is difficult to separate by filtering, which necessitates re-crystallisation from an organic solvent, generally an alcohol.

Further, in many applications, the products used must be in a form in which they must satisfy a number of requirements:
the product must be easy to manipulate;
the granulometric distribution of the product must exclude fine particles which generate dust;
the substance must have good flow properties and must not form lumps in temporary hopper type storage units or during use in a subsequent transformation process, or during long term storage in the usual packaging.

In order to satisfy the above requirements, the present invention provides a novel presentation of 10-phenothiazinylpropanoic acid and a process for obtaining it which can overcome the filtering problem.

More precisely, the present invention provides spherical agglomerates of 10-phenothiazinylpropanoic acid.

In the description of the present invention, the term "10-phenothiazinylpropanoic acid" includes 3-(10-phenothiazinyl)propanoic acid and similar products, i.e., products in which the benzene rings of the phenothiazinyl radical carry substituents provided that they do not modify the surface properties. Examples which can be cited are low alkyls ($C_1$–$C_4$), halogen atoms or a $CF_3$ radical.

The term "spherical" agglomerates means solid particles with a high degree of sphericity.

The process for preparing the spherical agglomerates of 10-phenothiazinylpropanoic acid is characterized by stirring a suspension of 10-phenothiazinylpropanoic acid in water in the presence of a liquid binder which is not miscible with water selected from esters of aliphatic or cycloaliphatic acids, aliphatic or cycloaliphatic alcohols, and aliphatic or cycloaliphatic ketones.

The agglomerates obtained in accordance with the invention have physicochemical properties which are peculiar to them. The essentially spherical particles have a diameter which can vary within a wide range. Size determination is carried out using image analysis.

Generally the particle size, expressed as the medial diameter ($d_{50}$), is from 50 $\mu$m to 3000 $\mu$m, preferably from 200 $\mu$m to 1200 $\mu$m and more preferably between 500 $\mu$m and 1000 $\mu$m. The medial diameter is defined as that at which 50% by weight of the particles have a diameter larger or smaller than the medial diameter.

FIG. 1 shows a photograph of the agglomerates of the invention taken using a microscope (magnification=16) which shows the spherical shape of the particles obtained.

A further characteristic of the agglomerates of the invention is that the fines ratio (particles of less than 100 $\mu$m) is low, preferably less than 0.5%, more preferably less than 0.1%.

In accordance with the process of the invention, spherical agglomerates of 10-phenothiazinylpropanoic acid are prepared by stirring a suspension of 10-phenothiazinylpropanoic acid in water in the presence of a liquid binder which is not miscible with water as defined above.

When selecting the liquid binder, an organic solvent is used in which the 10-phenothiazinylpropanoic acid is very slightly soluble, i.e., with a solubility of less than 5%, preferably less than 1%.

The liquid binder, selected from esters of aliphatic or cycloaliphatic acids, aliphatic or cycloaliphatic alcohols, and aliphatic or cycloaliphatic ketones, generally satisfies this requirement when its carbon condensation is at least 5. There is no upper limit to the number of carbon atoms provided that the binder remains liquid during granulation.

Thus in a variation of the process of the invention, a liquid which may be solid at ambient temperature (usually between 15° C. and 25° C.) but fusible under the granulation temperature conditions, is used. In this case, slight heating may be necessary during the granulation operation.

Particular examples of aliphatic acid esters used are n-propyl, isopropyl, n-butyl, isobutyl, sec-butyl, tert-butyl, n-pentyl, and isopentyl acetates.

Examples of aliphatic alcohols are isopentanol and octanol.

Regarding ketones, a particular example is cyclohexanone.

Of all of the binders cited above n-propyl acetate or isopropyl acetate are preferred.

The starting 10-phenothiazinylpropanoic acid may be a crystalline or ground product. The particle size, expressed as the medial diameter ($d_{50}$), can vary, for example from 1 $\mu$m to 100 $\mu$m.

The quantity of water with respect to the 10-phenothiazinylpropanoic acid is not critical; however, it is preferable to use suspensions corresponding to about 400 to 2000 $cm^3$ of water, preferably 800 to 1000 $cm^3$ per 100 g of 10-phenothiazinylpropanoic acid.

The mixture is stirred. The type of stirring is not critical, however it is preferable to use shear stirring using a Rushton® type turbine, for example.

The rate of stirring of the mixture must be sufficient to obtain a homogeneous suspension of 10-phenothiazinylpropanoic acid in water and a homogeneous dispersion of liquid binder. A rate of 500 to 800 rpm is generally used when operating in a 1 liter reactor.

The quantity of liquid binder with respect to the 10-phenothiazinylpropanoic acid is critical. Below a minimum quantity of liquid binder, there is no agglomeration; in contrast, if too great a quantity of liquid binder is used, the solid particles are dispersed in the liquid binder and they can easily deform.

For each liquid binder, the proportions between which spherical agglomerates are formed and remain stable can be carried out as follows.

Liquid binder is added dropwise to a suspension of 100 g of 10-phenothiazinylpropanoic acid in 900 $cm^3$ of water which is energetically stirred (rotation rate 700 rpm). Aliquots of the suspension are removed during addition and examined to determine the minimum quantity of liquid binder required to form spherical agglomerates. Liquid binder addition is continued to determine the quantity of liquid beyond which the spherical agglomerates begin to disaggregate.

As an indication, when using an aliphatic ester, the quantity to be used is advantageously between 0.4 and 0.7 g per g of 10-phenothiazinylpropanoic acid.

When using the process of the invention, it is not necessary to add liquid binder gradually; the quantity thereof which is necessary for formation of the spherical agglomerates can be added all at once to the stirred aqueous suspension of 10-phenothiazinylpropanoic acid.

In general, the spherical agglomerates form a few minutes after adding the liquid binder. The diameter of the agglomerates then increases approximately linearly with respect to the period of stirring then remains practically constant. It is thus possible to stop the growth of the agglomerates when they have reached the desired dimensions.

The spherical agglomerates can be separated from the formation medium using conventional solid/liquid separation techniques, preferably by filtering.

The constituents (water and liquid binder) of the liquid phase can be separated, for example by azeotropic distillation, and recycled to subsequent operations.

In accordance with the invention, it should be noted that the size of the agglomerates can be increased, after the agglomeration step and before the solid/liquid separation step, by adding a supplemental amount of 10-phenothiazinylpropanoic acid in suspension in water or by adding a supplemental amount of powdered 10-phenothiazinylpropanoic acid to the stirred medium containing the agglomerates. Solid 10-phenothiazinylpropanoic acid affixes itself to the surface of the formed grains and thus coats them with a solid layer. The quantity of 10-phenothiazinylpropanoic acid added can be 5% to 50% by weight of initially agglomerated the 10-phenothiazinylpropanoic acid.

The agglomerates obtained using the process of the invention can then be dried using conventional techniques which are known to the skilled person. Drying is generally carried out at atmospheric pressure or under reduced pressure (for example 50 to 100 mbar).

Drying is usually carried out in air at a temperature which can be from ambient temperature, for example 20° C., to a temperature of 100° C., preferably in the range 50° C. to 90° C.

Drying is continued to constant weight.

It is generally in the range 30 minutes to 12 hours, depending on the temperature selected.

The spherical agglomerates obtained using the process of the invention, which themselves constitute a further aspect of the invention, have good mechanical behaviour, attractive flow properties and are easy to manipulate. Further, they are easy to filter.

In a variation of the process of the invention, it has been discovered that 10-phenothiazinylpropanoic acid agglomerates more easily when the powder to be granulated is first moistened.

Thus 10-phenothiazinylpropanoic acid is thus taken up into an aqueous suspension.

The quantity of water used to carry out this operation depends on the granulometry of the starting powder. By way of indication, a quantity of water of 500 cm$^3$ to 2000 cm$^3$ is advantageously used per 100 g of 10-phenothiazinylpropanoic acid.

The powder and water are preferably brought into contact with stirring for a period varying, for example, between 5 minutes and 20 minutes.

Thus the moistened powder is separated using any suitable method, preferably by filtering, then the powder obtained undergoes an agglomeration step carried out using the process of the invention.

In a variation of the process of the invention, it has been discovered that it may be desirable, before the agglomeration operation of the invention, to carry out a first adsorption step using at least one organic solvent which is preferably slightly soluble in water (for example less than 5% by weight).

Examples of organic solvents which are suitable for this adsorption step are aliphatic ethers, preferably isopropyl ether, aliphatic esters, preferably n-propyl or isopropyl acetate, and aromatic hydrocarbons which may or may not be halogenated, preferably toluene or monochlorobenzene.

A mixture of organic solvents can also be used, either successively or simultaneously, optionally with intermediate steps of separation and resuspension.

The quantity of organic solvent(s) used is not critical and can vary a great deal. Thus it can represent 1% to 200% by weight of the 10-phenothiazinylpropanoic acid, preferably in the range 1% to 10%.

These products are adsorbed by dispersing them in an aqueous suspension of 10-phenothiazinylpropanoic with vigorous stirring.

The suspension is then separated, preferably by filtering.

The product obtained then undergoes an agglomeration process in accordance with the invention.

In a variation of the process of the invention, agglomeration can be encouraged by increasing the pH of the suspension of 10-phenothiazinylpropanoic acid, preferably to between 4 and 6.

To this end, any appropriate means can be used, more particularly by washing the starting product one or more times with water.

In a further variation of the process of the invention, which can optionally replace or supplement the preceding variation, agglomeration can be carried out in the presence of a mineral salt, preferably with a high ionic strength.

Examples of the salts are calcium salts, preferably calcium carbonate or calcium sulphate, and aluminum salts, preferably aluminium sulphate. Adding a salt encourages agglomeration.

The quantity of salt used is advantageously in the range 0.5% to 5% by weight of the 10-phenothiazinylpropanoic acid.

Thus the process of the invention results in agglomerates in which agglomeration can be facilitated by initial operations of moistening using an aqueous or organic liquid.

Different examples illustrating these implementations of the invention will now be given.

The following examples are given by way of illustration and are in no way limiting in nature.

EXAMPLE 1

The 10-phenothiazinylpropanoic acid was agglomerated in two successive steps Washing operation:

An aqueous suspension of 10% 10-phenothiazinylpropanoic acid (50 g of 10-phenothiazinylpropanoic acid in 450 g of water) was stirred at 600 revolutions per minute using a Rushton stirrer in a one liter reactor for 10 minutes.

The operation was carried out at ambient temperature.

The granulometric characteristics of the starting 10-phenothiazinylpropanoic acid were as follows:

$D_{10}$=0.9 μm;
$D_{50}$=3.4 μm;
$D_{90}$=12 μm;

The suspension was then filtered through a Büchner funnel then washed with one liter of water.

The filter cake was used in the next step.

Granulation operation:

This was carried out on 10-phenothiazinylpropanoic acid prepared during the preceding operation.

The 10-phenothiazinylpropanoic acid was granulated after adding 31.6 g of isopropyl acetate to the suspension.

After stirring for 2 h 5 minutes at 750 rpm, the agglomerates formed were oven dried at 70° C. at atmospheric pressure for 2 hours.

The granulometric characteristics of the granules obtained were as follows:
$D_{10}$=881 μm;
$D_{50}$=1130 μm;
$D_{90}$=1280 μm.

The number of fines was not quantifiable.

EXAMPLE 2

The 10-phenothiazinylpropanoic acid was agglomerated by prior adsorption of monochlorobenzene onto the 10-phenothiazinylpropanoic acid and by adding calcium carbonate to encourage agglomeration.

Adsorption operation:

The operation was carried out at ambient temperature.

The granulometric characteristics of the starting 10-phenothiazinylpropanoic acid were as follows:
$D_{10}$=0.9 μm;
$D_{50}$=3.4 μm;
$D_{90}$=12 μm;

0.5 g of monochlorobenzene was added to an aqueous suspension of 10% 10-phenothiazinylpropanoic acid (50 g of 10-phenothiazinylpropanoic acid in 450 g of water) and 10% of isopropyl acetate (50 g) stirred at 600 revolutions per minute, using a Rushton stirrer in a one liter reactor.

The system was stirred for 30 minutes.

The contents of the reactor were then filtered.

The filter cake was then washed with 1 liter of water.

Granulation operation:

The filter cake from the preceding experiment was added to 450 g of water and 0.3 g of calcium carbonate in the reactor.

The system was stirred for 1 hour. 30 g of isopropyl acetate was then added to the reactor.

The system was stirred for 1 hour.

0.2 g of calcium carbonate was then added to the reactor.

Granules with a size of less than one millimeter were then formed after I hour 30 minutes of stirring.

We claim:

1. Spherical agglomerates of 10-phenothiazinylpropanoic acid.

2. Agglomerates according to claim 1, having a medial diameter ($d_{50}$) in the range 50 μm to 3000 μm.

3. Agglomerates according to claim 1, having a fines ratio of less than 0.5%.

4. A process for preparing spherical agglomerates of 10-phenothiazinylpropanoic acid according to claim 1, comprising stirring a suspension of 10-phenothiazinylpropanoic acid in water in the presence of a liquid binder which is not miscible with water comprising esters of aliphatic or cycloaliphatic acids, aliphatic or cycloaliphatic alcohols, or aliphatic or cycloaliphatic ketones.

5. A process according to claim 4, wherein the aliphatic acid ester comprises n-propyl, isopropyl, n-butyl, isobutyl, sec-butyl, tert-butyl, n-pentyl or isopentyl acetates.

6. A process according to claim 5, wherein the non miscible liquid binder is n-propyl acetate or isopropyl acetate.

7. A process according to claim 4, wherein the aliphatic alcohol comprises isopentanol or octanol.

8. A process according to claim 4, wherein the ketone used is cyclohexanone.

9. A process according to claim 4, wherein a moistening step is first carried out on the starting powder by bringing the 10-phenothiazinylpropanoic acid into contact with water.

10. A process according to claim 4, wherein the 10-phenothiazinylpropanoic acid powder undergoes a first adsorption step using at least one organic solvent which is slightly soluble in water.

11. A process according to claim 10, wherein the organic solvent or solvents for said adsorption are aliphatic ethers, aliphatic esters, or aromatic hydrocarbons which may or may not be halogenated.

12. A process according to claim 11, wherein a mixture of organic solvents is used, either successively or simultaneously, optionally with intermediate steps of separation and resuspension.

13. A process according to claim 4, wherein agglomeration is encouraged by increasing the pH of the suspension.

14. A process according to claim 4, wherein a mineral salt is added to encourage agglomeration.

15. A process according to claim 14, wherein the added salt comprises calcium salts or aluminium salts.

16. Agglomerates according to claim 2, having a medial diameter ($d_{50}$) in the range of 200 μm to 1200 μm.

17. Agglomerates according to claim 16, having a medial diameter ($d_{50}$) in the range of 500 μm to 1000 μm.

18. Agglomerates according to claim 3, having a fines ratio of less than 0.1%.

19. The process according to claim 9, wherein the 10-phenothiazinylpropanoic acid is stirred with water.

20. The process according to claim 11, wherein the aliphatic ester is isopropyl ester, the aliphatic esters comprises n-propyl acetate or isopropyl acetate and the aromatic hydrocarbons comprise toluene or monochlorobenzene.

21. The process according to claim 13, wherein the pH of the suspension is preferably between 4 and 6.

22. The process according to claim 15, wherein the calcium salts comprise calcium carbonate or calcium sulphate and the aluminum salt is aluminum sulphate.

* * * * *